(12) United States Patent
Langland et al.

(10) Patent No.: US 11,719,541 B2
(45) Date of Patent: Aug. 8, 2023

(54) HYPER-LOCAL MAPPING OF ENVIRONMENTAL CONDITIONS

(71) Applicant: Aclima Inc., San Francisco, CA (US)

(72) Inventors: Todd Langland, Mill Valley, CA (US); Meghan Elizabeth Thurlow, San Francisco, CA (US); Robert Murphy, Alameda, CA (US); Davida Herzl, San Diego, CA (US)

(73) Assignee: Aclima Inc., San Francisco, CA (US)

( * ) Notice: Subject to any disclaimer, the term of this patent is extended or adjusted under 35 U.S.C. 154(b) by 0 days.

(21) Appl. No.: 16/682,871

(22) Filed: Nov. 13, 2019

(65) Prior Publication Data

US 2021/0140769 A1    May 13, 2021

(51) Int. Cl.
*G01C 21/00* (2006.01)
*G01N 33/00* (2006.01)

(52) U.S. Cl.
CPC ....... *G01C 21/005* (2013.01); *G01N 33/0062* (2013.01)

(58) Field of Classification Search
CPC .. G01C 21/005; G01C 21/30; G01N 33/0062; G01N 33/0047; G05D 1/0088; G01S 17/86; G01S 19/13; G01S 19/393; G01S 19/45
See application file for complete search history.

(56) References Cited

U.S. PATENT DOCUMENTS 5,323,152 A * 6/1994 Morita ................... G01S 19/45
340/988
9,494,694 B1 * 11/2016 Dong ..................... G01C 21/30
10,677,771 B2 * 6/2020 Dittberner .......... G01N 33/0047
(Continued)

FOREIGN PATENT DOCUMENTS

JP    2001319291    11/2001
JP    2002319086    10/2002
(Continued)

OTHER PUBLICATIONS

Apte et al., High-Resolution Air Pullution Mapping with Google Street View Cars: Exploiting Big Data, Environmental Science & Technology, pp. 6999-7008, Jun. 5, 2017.

*Primary Examiner* — Michael J Dalbo
*Assistant Examiner* — Kaleria Knox
(74) *Attorney, Agent, or Firm* — Van Pelt, Yi & James LLP

(57) ABSTRACT

A method for associating environmental data with map features is described. The method includes receiving sensor data and receiving position data. The sensor data is associated with each of a plurality of time intervals and is from at least one sensor on at least one mobile sensor platform. The position data is associated with the plurality of time intervals and is from the at least one mobile sensor platform. Trajectories and corrected locations of the mobile sensor platform are generated for the plurality of time intervals using the position data. A position of the mobile sensor platform is assigned to a corresponding map feature for each of the plurality of time intervals based on the trajectories and corrected locations. The sensor data is also processed to generate sensor data values for each of the plurality of time intervals. The sensor data values are assigned to the corresponding map feature of the position of the mobile sensor platform for each of the plurality of time intervals.

19 Claims, 8 Drawing Sheets

(56) References Cited

U.S. PATENT DOCUMENTS

| | | | |
|---|---|---|---|
| 2007/0010940 A1* | 1/2007 | Tan | G01S 19/393 |
| | | | 701/469 |
| 2008/0024323 A1 | 1/2008 | Kadaba | |
| 2012/0226391 A1 | 9/2012 | Fryer | |
| 2014/0350850 A1* | 11/2014 | Kmiecik | G01C 21/005 |
| | | | 701/487 |
| 2016/0178377 A1* | 6/2016 | Jung | G01S 19/13 |
| | | | 701/468 |
| 2016/0187144 A1* | 6/2016 | Modica | G01S 17/86 |
| | | | 382/154 |
| 2016/0189186 A1 | 6/2016 | Fabrikant | |
| 2018/0216942 A1 | 8/2018 | Wang | |
| 2019/0339709 A1* | 11/2019 | Tay | G05D 1/0088 |

FOREIGN PATENT DOCUMENTS

| | | |
|---|---|---|
| JP | 2008170249 | 7/2008 |
| JP | 2009506433 | 2/2009 |
| JP | 2010176136 | 8/2010 |
| JP | 2012233714 | 11/2012 |
| JP | 2017058235 | 3/2017 |
| JP | 2017142168 | 8/2017 |
| JP | 2018151265 | 9/2018 |
| JP | 2019164005 | 9/2019 |

* cited by examiner

| Pollutant | Value | Score |
|---|---|---|
| Black Carbon | 0.25 | 92 |
| CO | 0.04 | 96 |
| $CO_2$ | 408 | 94 |
| NO | 8.3 | 97 |
| $O_3$ | 6.6 | 97 |
| PM2.5 | 4.75 | 93 |
| Final Score | | 92 |
| Confidence Score | | 85 |

HYPER-LOCAL MAPPING OF ENVIRONMENTAL CONDITIONS

BACKGROUND OF THE INVENTION

Monitoring of environmental conditions includes measuring the levels of features in the surroundings, allowing detection of potentially harmful air pollution, radiation, greenhouse gases or other contaminants in the environment. Depending on the application, environmental monitoring systems can be mobile or stationary and can be used in outdoor or indoor settings. Monitoring of environmental conditions typically includes gathering environmental data. Environmental data includes detection and measurement of pollutants or contaminants such as nitrogen dioxide ($NO_2$), carbon monoxide (CO), nitrogen oxide (NO), ozone ($O_3$), sulphur dioxide ($SO_2$), carbon dioxide ($CO_2$), methane ($CH_4$), volatile organic compound (VOC), radiation and particulate matter. In order to assess the effects of such pollutants, it is desirable to associate environmental data sensing these pollutants particular times and/or geographic locations (homes, businesses, towns, etc.). Such an association would allow individuals and communities to evaluate the quality of their surroundings.

BRIEF DESCRIPTION OF THE DRAWINGS

Various embodiments of the invention are disclosed in the following detailed description and the accompanying drawings.

DETAILED DESCRIPTION

Figure 1:
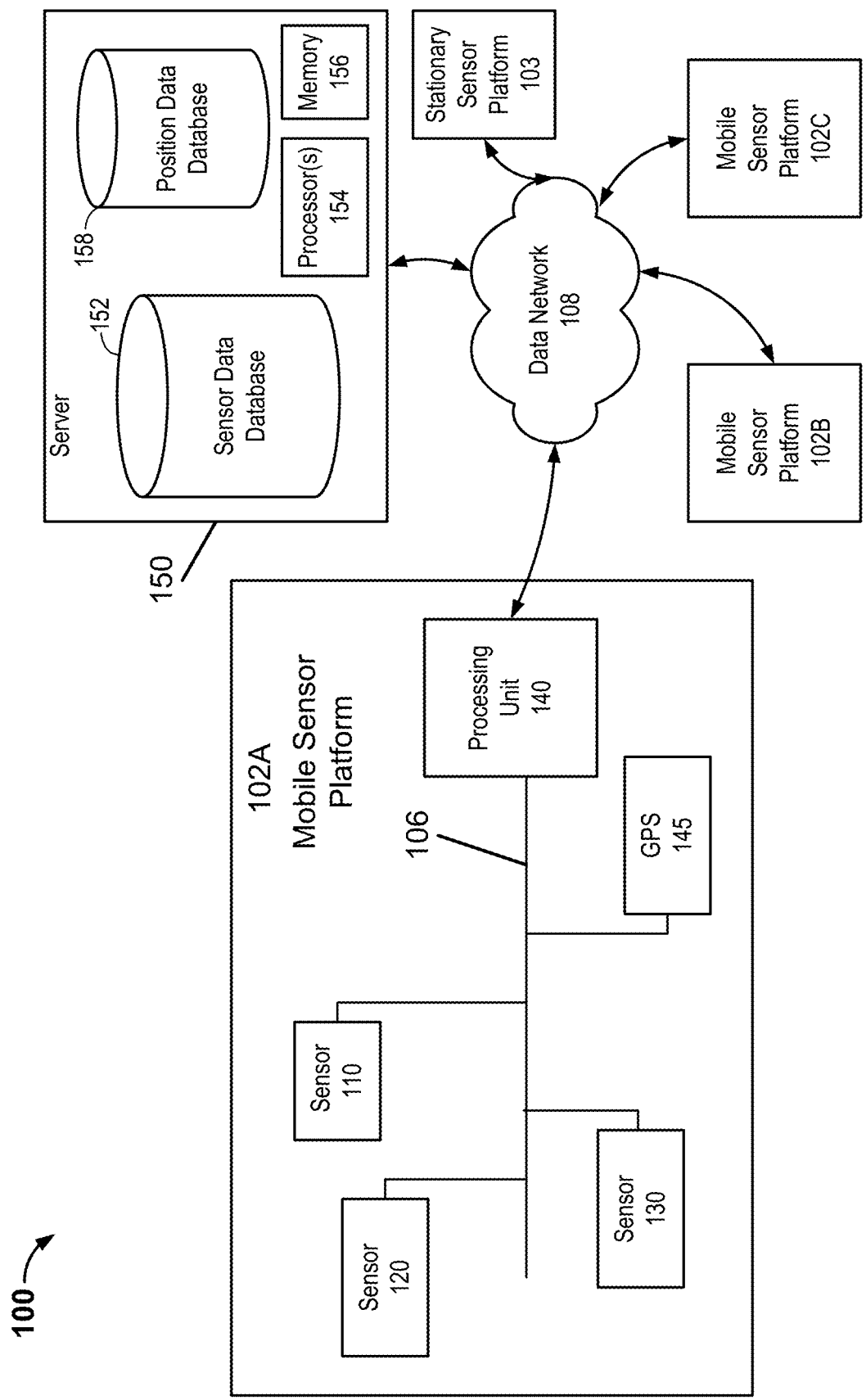
FIG. 1 depicts an embodiment of a system for capturing environmental data using mobile sensor platforms and associating the environmental data with map features.

The invention can be implemented in numerous ways, including as a process; an apparatus; a system; a composition of matter; a computer program product embodied on a computer readable storage medium such as a non-transitory computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Environmental data includes measurements of pollutants, contaminants and/or other components of the environment. Environmental quality can be assessed based on this environmental data and is a measure of the suitability of the surroundings for humans. An important aspect of environmental quality is air quality. However, other conditions in the environment may also be desired to be monitored. Environmental data thus includes but is not limited to measurements related to air quality (e.g. the presence or absence of various pollutants in the air) as well as other features of the surroundings. Environmental data may be captured using mobile and/or stationary sensor platforms and may include measurements of pollutants, contaminants, and/or other conditions. For example, environmental data may be gathered on nitrogen dioxide ($NO_2$), carbon monoxide (CO), nitrogen oxide (NO), ozone ($O_3$), sulphur dioxide ($SO_2$), carbon dioxide ($CO_2$), methane ($CH_4$), volatile organic compound (VOC), particulate matter, radiation, noise, temperature, other pathogens and/or other conditions that may affect humans. Environmental data may vary based upon a variety of factors such as the pollutant source, intrinsic spatial variations in pollutants, environmental conditions such as the wind, variations in terrain and the presence of man-made structures such as buildings. Consequently, environmental data may have significant local variations.

Individuals and communities may desire to assess the environmental quality in their geographic region. For example, an individual in an urban setting may desire to see how their city compares to other cities or how their neighborhood compares to other neighborhoods in the same city. In some instances, an individual may desire to investigate the environmental quality of their street or home address. To facilitate such individualized environmental quality assessments, environmental data is desired to be associated with map features. A map feature corresponds to a geographic location and is identifiable on a map. For example, a map feature may be a road or portion thereof (e.g. a road segment), a defined region that can be located on a map (e.g. a cell that may be identified by latitude and longitude boundaries), a location such as an address, a specific point such as a latitude and longitude and/or other geographic attribute that can be identified on a map.

However, associating environmental data with specific map features may have issues. It may be challenging to collect localized environmental data (e.g. data that varies within a city) to be associated with the map feature. If stationary sensors are used, an extremely large number of sensors must be deployed to collect data throughout the city. If mobile sensors are used, other issues arise. Coverage by a mobile sensor is temporally and spatially limited. Stated differently, a mobile sensor is limited to capturing data for a particular time at its current location. Data at the same location for a different time may not be captured by the sensor. Similarly, data in other locations for the particular time may not be captured by the sensor. Furthermore, correlating the sensor data with specific map features may be problematic. Accurately determining the location of a mobile sensor may be challenging. In urban settings, global positioning satellite (GPS) data may be unreliable, complicating the identification of the mobile sensor's position and the corresponding map features. Moreover, an individual may have difficulty determining the meaning of the environmental data. For example, a layman may not know whether a specified level of particulate matter or black carbon corresponds to good environmental quality or poor environmental quality. Consequently, a mechanism for determining environmental quality and localized variations thereof as well as for assessing the environmental quality is desired.

A technique for associating environmental data with map features is described. The method includes receiving sensor data and receiving position data. The sensor data is associated with each of a plurality of time intervals and is from sensor(s) on mobile sensor platform(s). The position data is associated with the time intervals and is from the mobile sensor platform(s). Trajectories and corrected locations of the mobile sensor platform(s) are generated using the position data. Based on the trajectories and corrected locations, a position of the mobile sensor platform(s) is assigned to a corresponding map feature for each time interval. For example, the map feature may be a road segment or cell (region or area). The position of the mobile sensor platform may be assigned to the road segment or cell. The sensor data is also processed to generate sensor data values for each of the time intervals. The sensor data values are assigned to the corresponding map feature of the position of the mobile sensor platform for each time interval.

In some embodiments, mobile sensor platform(s) collect the position and sensor data and send the data to a server. The server processes the sensor data to provide sensor data values, determines the trajectories and corrected locations, assigns the positions to the mobile sensor platform, assigns the position to the corresponding map features, and associates the sensor data values with the corresponding map feature assigned to the position. In some embodiments, some or all of the processing may occur elsewhere. For example, the mobile sensor platform may perform at least some processing on the sensor data before sending the sensor data to the server system for further processing. In some embodiments, the mobile sensor platform may also perform at least some processing on the position data before sending the position data to the server.

In some embodiments, environmental data for a map location is generated based on the sensor data values assigned to the map features near the map location. The map location might be a real estate parcel, multiple real estate parcels (e.g. a neighborhood), an address such as a home or apartment, a business or other physical locale. The sensor data values for map features within a particular distance (e.g. radius) of the map location may be weighted and weighted averages determined. For example, sensor data values may be associated with road segments (map features). Environmental data may be desired for an address (map location), such as a home or apartment complex. Sensor data values for road segments within the particular distance of the address may be weighted. For example, the weighting may be based upon the fraction of the map feature within the radius of the map location. In some embodiments, a distance-based Gaussian weighted average may be used. In some embodiments, other and/or additional weighting mechanisms, such as the distance between the data point and the center of the map location, might be employed. A weighted average is calculated for the sensor data values of each sensor. These weighted averages may be considered the sensor data values for the map location. Thus, map features such as cells or road segments having a larger fraction close to (within the particular distance of) the map location may contribute more to the weighted averages. These weighted averages allow for the surroundings of a particular map location to be taken into account when generating environmental data for and determining the environmental quality of the map location.

In some embodiments, the map features may be fixed in size. For example, the map feature may be a road segment or cell (region) having a predefined length or a predefined area. In some embodiments, the predefined length or area may vary between road segments or cells, respectively. For example, a road segment in an urban area may be shorter than a road segment in a rural area, or vice versa. However, the map features do not change. In other embodiments, the map features may be dynamically adjusted. For example, the area of the cell and/or length of the road segment may change. In some embodiments, the road segment length may be different for different sensors (e.g. for different pollutants) and/or may change based upon other criteria including but not limited to the time of day at which data are captured, the weather (e.g. prevailing winds) and topography (e.g. density of surrounding structures). For example, a sensor having a longer response time might have a longer road segment length.

Receiving the sensor data, receiving the position data, generating the trajectories and corrected locations, assigning the positions, processing sensor data and assigning sensor data values to corresponding map features may be repeated. For example, one or more mobile sensor platforms may traverse similar routes and collect data for the same geographic region. Stated differently, mobile sensor platforms may make multiple passes over the same map features. For various locations, there may be a distribution of environmental conditions, which may vary over time. Multiple passes for data collection allows variations in environmental conditions to be randomly or systematically sampled. Repeatedly collecting data may thus increase the level of confidence in the accuracy of the environmental data collected by the sensors on the mobile sensor platform. Thus, multiple passes by the same or different mobile sensor platforms may be used to collect sensor data for various positions.

Based on the sensor data values assigned to the map features, an environmental score may be determined. In some embodiments, the environmental score may be determined for some or all of the map features and/or for other locations. The environmental score may be a relative score based upon the sensor data values for the region. For example, the region may be defined as the city limits, a particular set of latitudes and longitudes, or using another mechanism. Thus, an individual may easily compare the environmental score of interest with other environmental scores in the same area. In some embodiments, the relative score may be based upon sensor data values for distal regions. For example, the relative scores of a particular city may be based on and compared with those of another city. In some embodiments, the relative scores may be based on other criteria. In some embodiments, the scores are standardized. For example, particular ranges of sensor data values for each sensor may correspond to a particular score. A score may also be generated for a particular map location, such as an address, using the environmental data generated as discussed above. Similarly, a confidence score may be provided for various map features or locations. The confidence score may be based upon the number of passes for the map features. For example, the greater the number of distinct times (e.g. different days and/or different times of day) a mobile sensor platform collects data at a location or map feature may increase the confidence that the sensor data values accurately represent the environmental conditions at the location or map feature. Consequently, the environmental data and corresponding score may evolve over time.

Using the techniques described herein, a sparse network of sensor platforms (mobile and, optionally, stationary), can provide hyper-local environmental data. More specifically, environmental data can be collected at and assigned to map features as described above, environmental data can be generated for particular locations based upon data including data for surrounding map features, and environmental and confidence scores provided for evaluating the environmental data. The map features may be hyper-local in nature. For example, hyper-local road segments (map features) may be less than or equal to two hundred meters in length in some embodiments. Hyper-local road segments may be less than or equal to one hundred meters in some embodiments. In some embodiments, hyper-local road segments may be less than or equal to thirty meters. In some embodiments, hyper-local road segments of twenty meters or less may be used. Because distinct environmental data can be collected for and assigned to map features of such small sizes, variations in the environmental data on these scales can be measured and analyzed. Thus, hyper-local variations in environmental quality may be determined.

Because mobile sensor platforms are used, a sparse network of sensors can be considered to result in the hyper-local environmental data. For example, the same mobile sensor platform may repeatedly traverse particular map features on a single route or on repeated passes of the same route or different routes. Consequently, a large number of stationary sensor platforms need not be deployed throughout a community in order to obtain environmental data for the community. Instead a relatively small number of mobile sensor platform(s) may traverse route(s) through the community in order to obtain sensor data. The mobile sensor platform(s) may also traverse the routes on different days, at different times of the day, and/or at different times of year to provide better confidence in the environmental data. In some embodiments, mobile platforms may be re-deployed in response to identified changes in the area (such as a new structure being built or a new source of pollution being identified) or based on other criteria (such as based on periodic time intervals). Thus, hyper-local environmental data may be obtained, updated and associated with hyper-local map features using a relatively sparse network of mobile sensor platforms.

FIG. 1 depicts an embodiment of a system 100 for collecting and processing environmental data. System 100 includes multiple mobile sensor platforms 102A, 102B, 102C and server 150. In some embodiments, system 100 may also include one or more stationary sensor platforms 103, of which one is shown. Stationary sensor platform 103 may be used to collect environmental data at a fixed location. The environmental data collected by stationary sensor platform 103 may supplement the data collected by mobile sensor platforms 102A, 102B and 102C. Thus, stationary sensor platform 103 may have sensors that are the same as or analogous to the sensors for mobile sensor platforms 102A, 102B and 102C. In other embodiments, stationary sensor platform 103 may be omitted. Although a single server 150 is shown, multiple servers may be used. The multiple servers may be in different locations. Although three mobile sensor platforms 102A, 102B and 102C are shown, another number are typically present. Mobile sensor platforms 102A, 102B and 102C and stationary sensor platform(s) 103 may communicate with server 150 via a data network 108. The communication may take place wirelessly.

Mobile sensor platforms 102A, 102B and 102C may be mounted in a vehicle, such as an automobile or a drone. In some embodiments, mobile sensor platforms 102A, 102B and 102C are desired to stay in proximity to the ground to be better able to sense conditions analogous to what a human would experience. Mobile sensor platform 102A includes a bus 106, sensors 110, 120 and 130. Although three sensors are shown, another number may be present on mobile sensor platform 102A. In addition, a different configuration of components may be used with sensors 110, 120 and 130. Each sensor 110, 120 and 130 is used to sense environmental quality and may be of primary interest to a user of system 100. For example, sensors 110, 120 and 130 may be gas sensors, volatile organic compound (VOC) sensors, particulate matter sensors, radiation sensors, noise sensors, light sensors, temperature sensors, noise sensors or other analogous sensors that capture variations in the environment. For example, sensors 110, 120 and 130 may be used to sense one or more of $NO_2$, CO, NO, $O_3$, $SO_2$, $CO_2$, VOCs, CH4, particulate matter, noise, light, temperature, radiation and other compounds. In some embodiments, sensor 110, 120 and/or 130 may be a multi-modality sensor. A multi-modality gas sensor senses multiple gases or compounds. For example, if sensor 110 is a multi-modality $NO_2/O_3$ sensor, sensor 110 might sense both $NO_2$ and $O_3$ together.

Although not shown in FIG. 1, other sensors co-located with sensors 110, 120 and 130 may be used to sense characteristics of the surrounding environment including, in some instances, other gases and/or matter. Such additional sensors are exposed to the same environment as sensors 110, 120 and 130. In some embodiments, such additional sensors are in close proximity to sensors 110, 120 and 130, for example within ten millimeters or less. In some embodiments, the additional sensors may be further from sensors 110, 120 and 130 if the additional sensors sample the same packet of air inside of a closed system, such as a system of closed tubes. In some embodiments, temperature and/or pressure are sensed by these additional sensors. For example, an additional sensor co-located with sensor 110 may be a temperature, pressure and relative humidity (T/P/RH) sensor. These additional co-located sensors may be used to calibrate sensors 110, 120 and/or 130. Although not shown, sensor platform 102A may also include a manifold for drawing in air and transporting air to sensors 110, 120 and 130 for testing.

Sensors 110, 120 and 130 provide sensor data over bus 106, or via another mechanism. In some embodiments, data from sensors 110, 120 and 130 incorporates time. This time may be provided by a master clock (not shown) and may take the form of a timestamp. Master clock may reside on sensor platform 102A, may be part of processing unit 140, or may be provided from server 150. As a result, sensors 110, 120 and 130 may provide timestamped sensor data to server 150. In other embodiments, the time associated with the sensor data may be provided in another manner. Because sensors 110, 120 and 130 generally capture data at a particular frequency, sensor data is discussed as being associated with a particular time interval (e.g. the period associated with the frequency), though the sensor data may be timestamped with a particular value. For example, sensors 110, 120 and/or 130 may capture sensor data every second, every two seconds, every ten seconds, or every thirty seconds. The time interval may be one second, two seconds, ten seconds or thirty seconds. The time interval may be the same for all sensors 110, 120 and 130 or may differ for different sensors 110, 120 and 130. In some embodiments, the time interval for a sensor data point is centered on the timestamp. For example, if the time interval is one second and a timestamp is t1, then the time interval may be from t1−0.5 seconds to t1+0.5 seconds. However, other mechanisms for defining the time interval may be used.

Sensor platform 102A also includes a position unit 145 that provides position data. In some embodiments, position unit 145 is a global positioning satellite (GPS) unit. Consequently, system 100 is described in the context of a GPS unit 145. The position data may be time-stamped in a manner analogous to sensor data. Because position data is to be associated with sensor data, the position data may also be considered associated with time intervals, as described above. However, in some embodiments, position data (e.g. GPS data) may be captured more or less frequently than sensor data. For example, GPS unit 145 may capture position data every second, while sensor 130 may capture data every thirty seconds. Thus, multiple data points for the position data may be associated with a single thirty second time interval. The position data may be processed as described below.

Optional processing unit 140 may perform some processing and functions for data from sensor platform 104, may simply pass data from sensor platform 104 to server 150 or may be omitted.

Mobile sensors platforms 102B and 102C are analogous to mobile sensor platform 102A. In some embodiments, mobile sensor platforms 102B and 102C have the same components as mobile sensor platform 102A. However, in other embodiments, the components may differ. However, mobile sensor platforms 102A, 102B and 102C function in an analogous manner.

Server 150 includes sensor data database 152, processor(s) 154, memory 156 and position data database 158. Processor(s) 154 may include multiple cores. Processor(s) 154 may include one or more central processing units (CPUs), one or more graphical processing units (GPUs) and/or one or more other processing units. Memory 156 can include a first primary storage, typically a random access memory (RAM), and a second primary storage area, typically a non-volatile storage such as solid state drive (SSD) or hard disk drive (HDD). Memory 156 stores programming instructions and data for processes operating on processor(s) 154. Primary storage typically includes basic operating instructions, program code, data and objects used by processor(s) 154 to perform their functions. Primary storage devices (e.g., memory 156) may include any suitable computer-readable storage media, described below, depending on whether, for example, data access needs to be bi-directional or uni-directional Sensor data database 152 includes data received from mobile sensor platforms 102A, 102B and/or 102C. After capture by mobile sensor platform 102A, 102B and/or 102C, sensor data stored in sensor data database 152 may be operated on by various analytics, as described below. Position data database 158 stores position data received from mobile sensor platforms 102A, 102B and/or 102C. In some embodiments, sensor data database 152 stores position data as well as sensor data. In such embodiments, position data database 158 may be omitted. Server 150 may include other databases and/or store and utilize other data. For example, server 150 may include calibration data (not shown) used in calibrating sensors 110, 120 and 130.

System 100 may be used to capture, analyze and provide information regarding hyper-local environmental data. Mobile sensor platforms 102A, 102B and 102C may be used to traverse routes and provide sensor and position data to server 150. Server 150 may process the sensor data and position data. Server 150 may also assign the sensor data to map features corresponding to the locations of mobile sensor platforms 102A, 102B and 102C within the same time interval as the sensor data was captured. As discussed above, these map features may be hyper-local (e.g. one hundred meter or less road segments or thirty meter or less road segments). Thus, mobile sensor platforms 102A, 102B and 102C may provide sensor data that can capture variations on this hyper-local distance scale. Server 150 may provide the environmental data, a score, confidence score and/or other assessment of the environmental data to a user. Thus, using system 100 hyper-local environmental data may be obtained using a relatively sparse network of mobile sensor platforms 102A, 102B and 102C, associated with hyper-local map features and processed for improved understanding of users.

Figure 2:
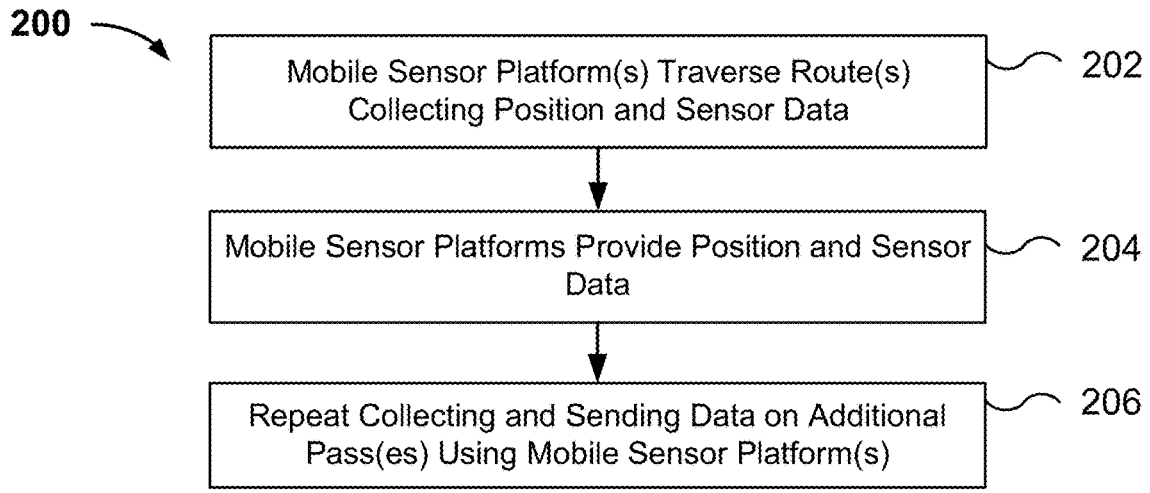
FIG. 2 depicts an embodiment of a method for capturing environmental data using mobile sensor platforms.

FIG. 2 depicts an exemplary embodiment of method 200 for capturing environmental data using mobile sensor platforms, such as mobile sensor platforms 102A, 102B and/or 102C. Method 200 is described in the context of system 100, but may be performed using other systems. For clarity, only some portions of method 200 are shown. Although shown in a sequence, in some embodiments, processes may occur in parallel and/or in a different order.

Mobile sensor platforms traverse routes in a geographic region, at 202. While traversing the routes, the mobile sensor platforms collect not only sensor data, but also position data. For example, a mobile sensor platform may sense one or more of $NO_2$, CO, NO, $O_3$, $SO_2$, $CO_2$, $CH_4$, VOCs, particulate matter, other compounds, radiation, noise, light and other environmental data at various times during traversal of the route. Other environmental characteristics, including but not limited to temperature, pressure, and/or humidity may also be sensed at 202. In addition, the time corresponding to the environmental data is also captured. The time may be in the form of a timestamp for the sensor data (sensor timestamp), which may correspond to a particular time interval. Different sensors on the mobile sensor platform may capture the environmental data at different times and/or at different frequencies. Also at 202 the mobile sensor platforms capture position data, for example via a GPS unit. The position data may include location (as indicated by a GPS unit), velocity and/or other information related to the geographic location of the mobile sensor platform. In some embodiments, position data from other sources, such as acceleration, may be captured from by the vehicle or another source. The position data may include a timestamp (position timestamp) or other indicator of the time at which the position data is captured.

The mobile sensor platforms provide the position and sensor data to a server, at 204. In some embodiments, mobile sensor platforms provide this data substantially in real time, as the mobile sensor platforms traverse their routes at 202.

Thus, the position and sensor data may be transmitted wirelessly to the server. In some embodiments, some or all of the position and/or sensor data is stored at the mobile sensor platform and provided to the server at a later time. For example, the data may be transferred to the server when the mobile sensor platform returns to its base. In some embodiments, the mobile sensor platform may process the sensor data and/or position data prior to sending the sensor and/or position data to the server. In other embodiments, the mobile sensor platform provides little or no processing. The sensor data and position data may be sent at the same time or may be sent separately.

At 206, the route traversal and data collecting of 202 and data sending of 204 are repeated. Thus, the mobile sensor platforms may traverse the same or different routes at 206. In either case, multiple passes of the same geographic locations, and thus multiple passes of the same corresponding map features, are made at 206. In some embodiments, the repetition at 206 may be periodic (e.g. approximately every week, month or other time period). In some embodiments, the repetition at 206 may be performed based on other timing. In some cases, the same mobile sensor platform is sent on the same route and/or collects data for the same map features. In some embodiments, different mobile sensor platforms collect data may be used for the same routes and/or map features. Also at 206, steps 202 and 204 may be performed multiple times. Thus, at 206, data for a particular region may be aggregated over time.

Figure 3A:
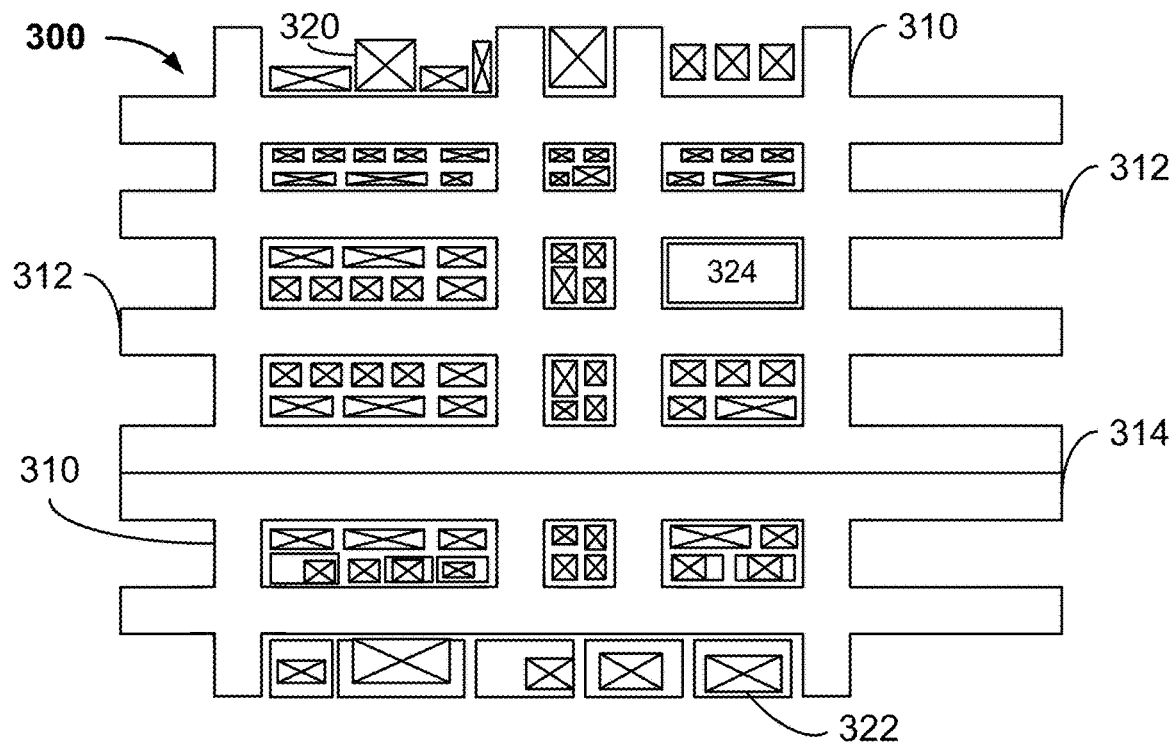
FIGS. 3A-3C illustrate a particular region and the embodiment of routes that may be traversed using a method for capturing environmental data using mobile sensor platforms.
Figure 3B:
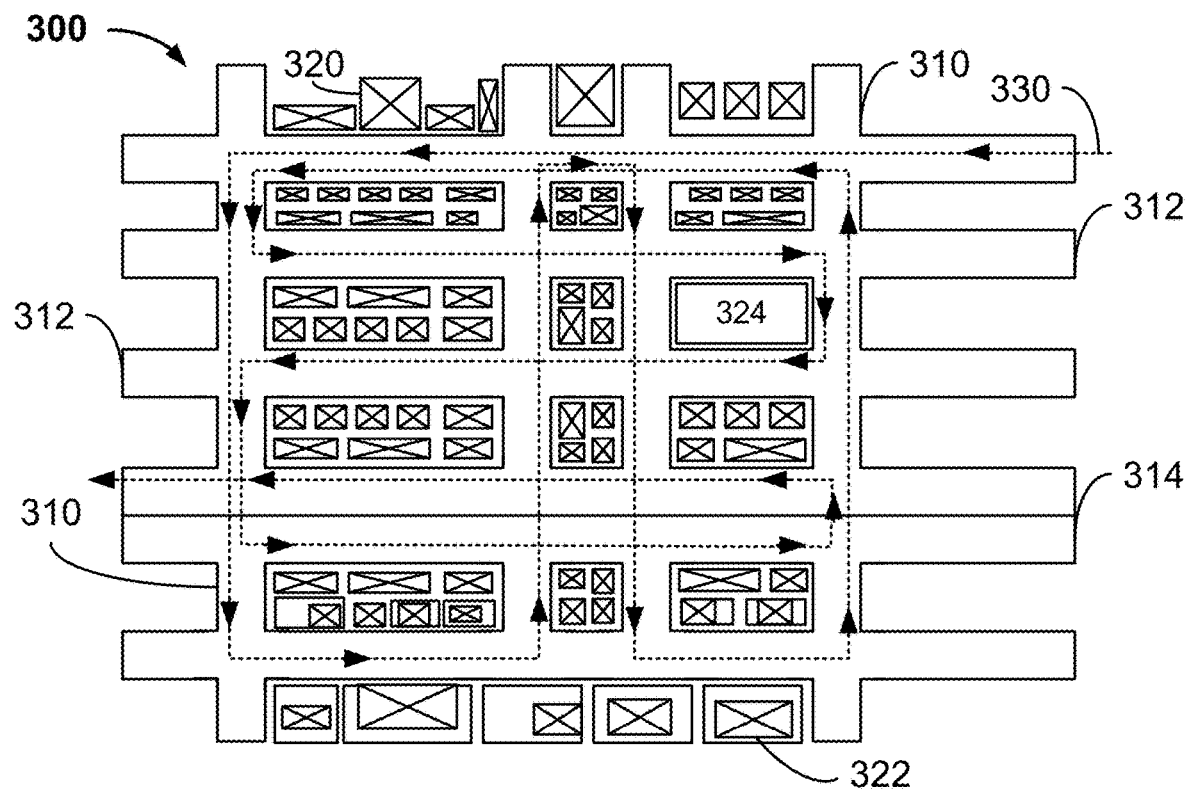
Figure 3C:
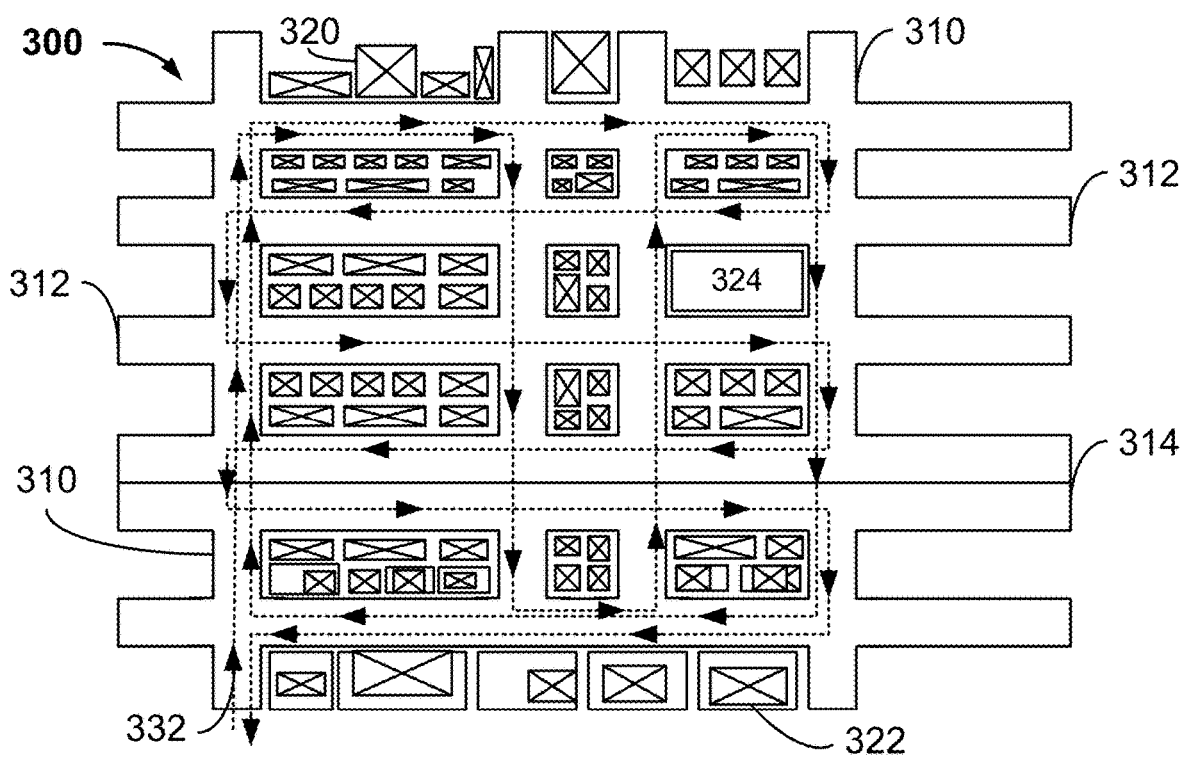

For example, FIGS. 3A-3C illustrate a particular geographic region and the routes that may be traversed using method 200. A map 300 corresponding to the geographic region is shown in FIG. 3A. Map 300 may be an open source map or generated by another mapping tool. Map 300 includes streets 310 (oriented vertically on the page) and 312 (oriented horizontally on the page); larger street/highway 314, structures 320 and 322 and open area 324. For simplicity, only one of each structure 320 and 322 is labeled. Open area 324 may correspond to a park, vacant lot or analogous item. As can be seen in FIG. 3A, the density and size of structures 320 and 322 vary across map 300. Similarly, the density and size of streets 312, 314 and 320 also varies. In addition, structures 322 are more clearly separated by open regions, which may correspond to a yard or analogous area.

FIG. 3B illustrates map 300 as well as route 330 that may be traversed by a mobile sensor platform, such as mobile sensor platform 102A. At 202, mobile sensor platform 102A may traverse route 330. As can be seen in FIG. 3B, the route 330 includes a portion of each street 312 and 314 in map 300. Some portions of some streets are traversed multiple times for the same route 330. In some embodiments, this is still considered a single pass of these streets. As mobile sensor platform 102A traverses route 330 at 202, sensor data is captured by sensors 110, 120 and 130. Also at 202, position data is captured by GPS unit 145 throughout route 330. In some embodiments, the vehicle carrying mobile sensor platform 102A travels sufficiently slowly while traversing route 330 that sensor data and position data can be accurately captured for particular position(s). In some embodiments, mobile sensor platform 102A travels at a velocity that allows for multiple sensor data points for each map feature. Mobile sensor platform 102A also sends position and sensor data to server 150 at 204. This may be done while mobile sensor platform 102A traverses route 330 or at a later time. Other mobile sensor platforms 102B and/or 102C may also traverse the same or different routes and send data to server 150 at 202 and 204. Thus, multiple mobile sensor platforms may be used in method 200.

At 206, mobile sensor platform 102A and/or other mobile sensor platform(s) 102B and 102C repeat the route traversal, data collection and sending of the position and sensor data. In some cases, mobile sensor platform(s) 102A, 102B and/or 102C follow route 330 again. In some cases, mobile sensor platform(s) 102A, 102B and/or 102C traverses a different route. For example, FIG. 3C depicts map 300 with another route 332. As part of 206, mobile sensor platform(s) 102A, 102B and/or 102C may traverse route 332, collecting position and sensor data at 206 (repeating 202). In some embodiments, the vehicle carrying mobile sensor platform(s) 102A, 102B and/or 102C travels sufficiently slowly while traversing route 332 that sensor data and position data can be accurately captured for particular position(s). In some embodiments, mobile sensor platform(s) 102A, 102B and/or 102C travels at a velocity that allows for multiple sensor data points for each map feature (described below). Mobile sensor platform(s) 102A, 102B and/or 102C send sensor and position data to server 150 at 206 (repeating 204) during or after traversing route 330 and/or route 332.

Thus, using method 200, sensor and position data may be captured for regions of a map. The sensor data and position data may be provided to server 150 or other component for processing, aggregation and analysis. Sensor data and position data are sensed sufficiently frequently using method 200 that variations environmental quality on the hyper-local scales may be reflected in the sensor data. Method 200 may be performed using a relatively small number of mobile sensor platforms. Consequently, efficiency of data gathering may be improved while maintaining sufficient sensitivity in both sensor and position data.

Figure 4:
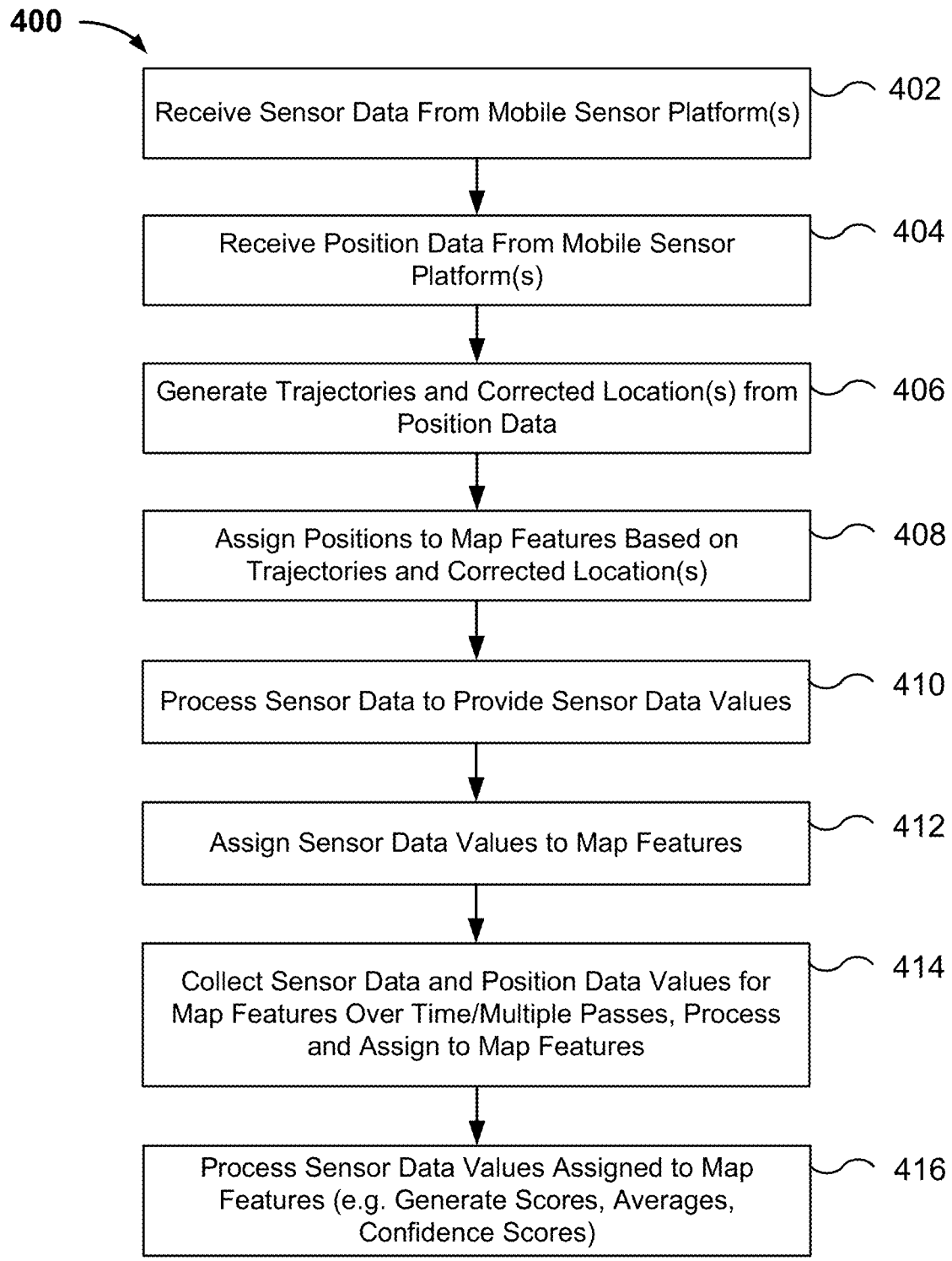
FIG. 4 depicts an embodiment of a method for associating environmental data with map features.

FIG. 4 depicts an embodiment of method 400 for associating sensor data with map features. Method 400 is described in the context of system 100 and map 300. However, method 400 may be used in connection with other data collection and/or processing systems. For clarity, only some portions of method 400 are shown. Although shown in a sequence, in some embodiments, processes may occur in parallel and/or in a different order.

Sensor data is received from the mobile sensor platform(s), at 402. The sensor data was captured by one or more sensors on the mobile sensor platform(s) and may be received at a server. Each data point in the sensor data may have a timestamp (i.e. a sensor timestamp). Thus, the sensor data is associated with time intervals. The amount of time between sensor timestamps may correspond to the time interval. In some embodiments, different sensors may have different time intervals. The time intervals may be based upon the response time, or time constant, of the sensor. The response time of a sensor may be affected by how rapidly a flow moves through the sampling lines for a sensor as well as the time taken by the sensor itself to complete an observation. For example, a sensor that takes a relatively long time (e.g. up to thirty seconds) to collect data (e.g. a long time constant) may have a thirty second time interval, while a sensor that can more rapidly sense data (e.g. every two seconds, for a shorter response time) may have a two second time interval. In embodiments in which sensor data from stationary sensor platforms is also used, the sensor data from stationary platforms is also received at 402.

Position data is received from mobile sensor platform(s), at 404. The position data may be gathered by a GPS unit and provided to a server. Each data point of the position data may have a timestamp (position timestamp). The sensor timestamps in the sensor data may differ from the position timestamps in the position data because sensor data and position data may be captured data different times. For stationary sensor platforms, position data need not be sent at 404, but instead may be stored, for example at the server. Thus, data collected and sent using method 200 may be received at 402 and 404.

Trajectories and corrected locations for the mobile sensor platform are generated using the position data, at 406. As discussed above, locations provided directly from a GPS unit may be unreliable in urban settings. For example, a vehicle traveling down a first street may have a first series of GPS data points corresponding to the first street, then have a GPS data point located on a second street, and then a second series of GPS data points for the first street. If the GPS data is not corrected, an erroneous position (e.g. the second street) may be associated with the sensor data. Thus, at 406, the GPS data is used to generate a trajectory. In some embodiments, the position timestamps and GPS data points (the combination of which may be considered analogous to a velocity/speed and direction) are used to establish the trajectory. The trajectory in combination with other GPS data is used to provide a corrected location. In the example above, the trajectory is along the first street in the direction(s) indicated by the first and second series of GPS data points. The corrected location for the erroneous position is on the first street between the two series of points. Thus, a more accurate determination of the position of the mobile sensor platform(s) can be made at 406. In embodiments in which the GPS or other data used is determined to be sufficiently accurate, 406 may be omitted.

Based on the corrected location and trajectory, the position of the mobile sensor platform is assigned to a corresponding map feature for each time interval, at 408. For example, the corrected location of mobile sensor platform may be assigned to a particular segment of a road, to a particular area (cell), to a particular address, particular latitude and longitude ranges, or other section of a map for the corresponding position timestamp.

Figure 5A:
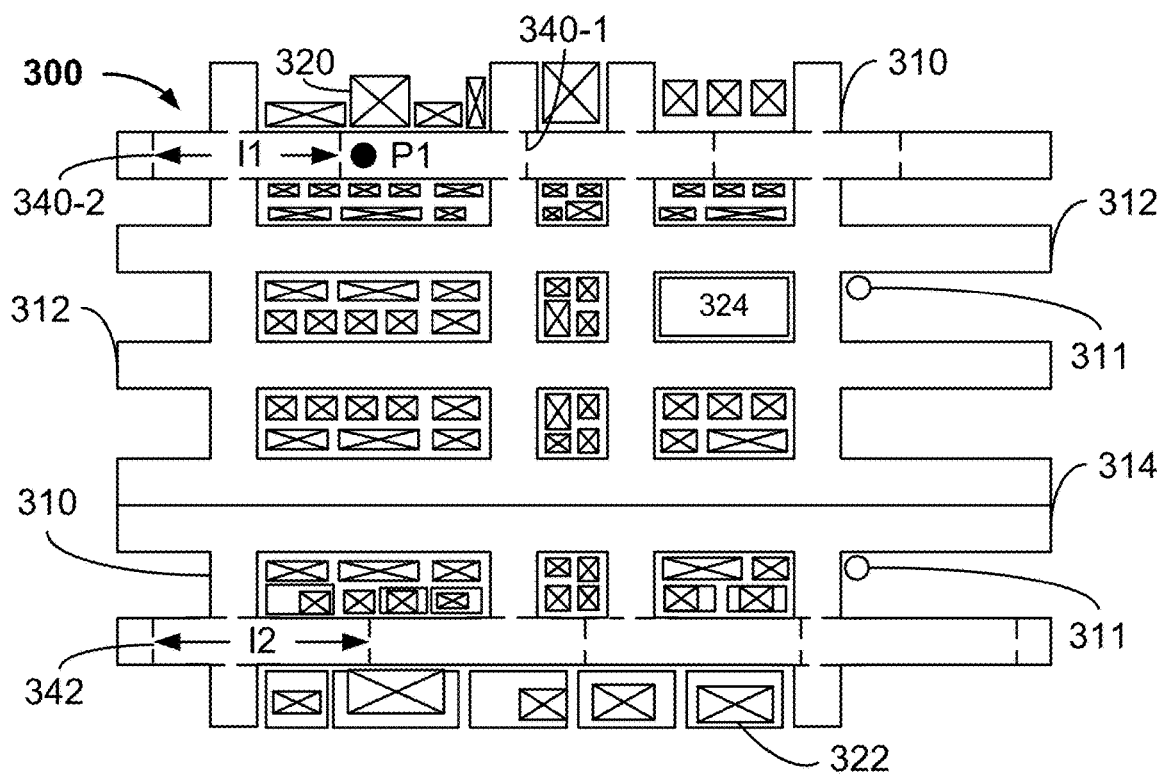
FIGS. 5A-5B depict embodiments of map features with which environmental data may be associated.
Figure 5B:
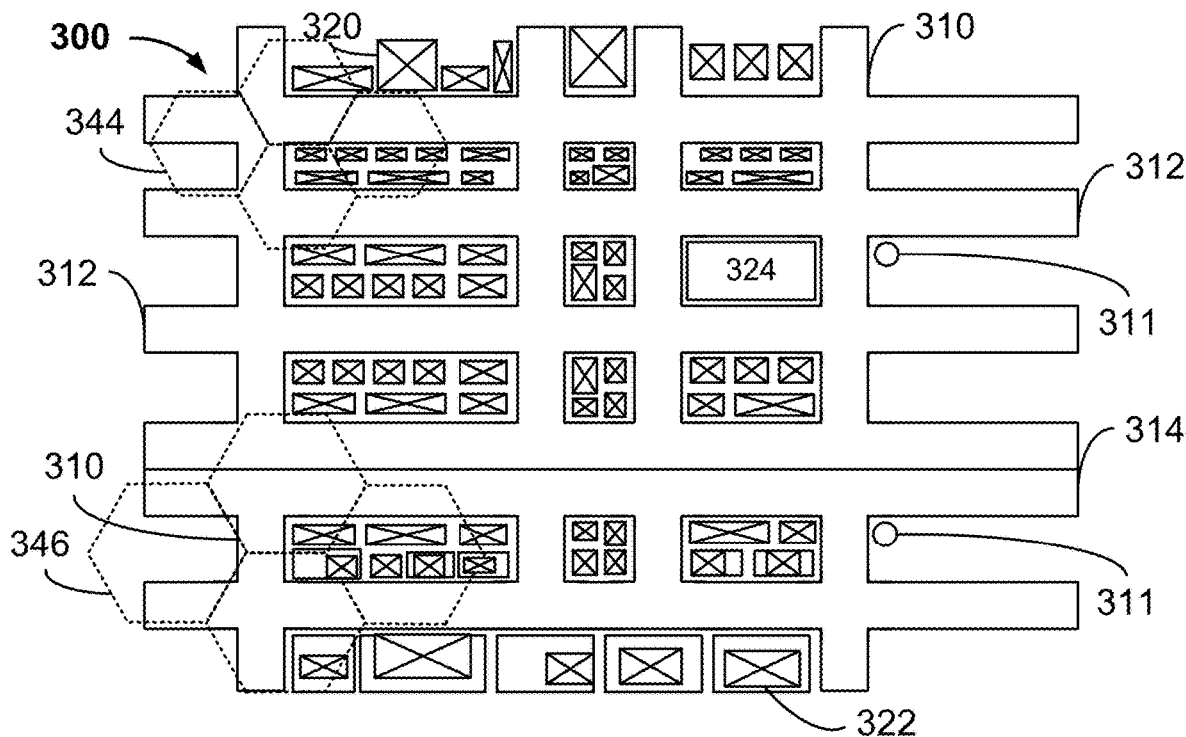

For example, FIGS. 5A and 5B depict map 300 in which different map features are shown. In FIG. 5A, the map features used are road segments 340-1 and 340-2 (collectively 340) and road segment 342. In the embodiment shown, the road segments 340 and 342 have lengths 11 and 12, respectively, that differ. In other embodiments, all road segments might have the same length. The lengths of the road segment may be static or dynamically changed. For example, road segments having different lengths may be used for different sensors. In some embodiments, the road segment length may be dynamically changed based on other criteria. For example, an increase in wind speed may result in a change in the length of the road segment. FIG. 5B depicts map 300 in which cells 344 and 346 are used for map features. Cells may be readily scaled up or down in size. Cells may also cover a portion of the area not readily reachable by a mobile sensor platform driven on roads by a vehicle, such as structures 320 and/or 322. In the embodiment shown, cells 344 and 346 have areas that differ. In other embodiments, all cells might have the same size and shape. The sizes and shapes of the cells may be static or dynamically changed. Although shown as regular hexagons, in other embodiments, cells having other shapes may be utilized. Also shown in FIGS. 5A and 5B are stationary sensor platforms 311.

The sensor data received at 402 is processed to generate sensor data values, at 410. For example, sensor data may be calibrated and converted to levels of the particular material being sensed. Thus, data from a black carbon sensor may be processed and converted to a particular level of black carbon. Data from a NO sensor may be processed using the appropriate calibration for that sensor and converted a level, such as parts per million (ppm), of NO. In some embodiments, 410 may also be performed for sensor data from stationary sensor platforms 103 and/or 311. Thus, in some embodiments sensor data from both mobile sensor platforms and stationary sensor platforms may be processed.

The sensor data values for each time interval are assigned to the corresponding map features of the position of the mobile sensor platform, at 412. Thus, the sensor data value(s) for a particular time interval are assigned to the map feature(s) that the position(s) for the corresponding time intervals were assigned to at 408. Multiple sensor data values may be assigned to the same map feature. For example, three sensor data values with three different sensor timestamps may be assigned to the same map feature if the corresponding positions of the mobile sensor platform for all three sensor data values are assigned to a single map feature. Also at 412, sensor data from stationary sensor platforms 311 may be assigned to a map feature including or adjacent to the stationary sensor platform.

At 414, receiving the sensor and position data, generating trajectories and corrected locations, assigning positions to map features, processing sensor data and assigning sensor data to map features are repeated. Thus, 402, 404, 406, 408, 410 and 412 are repeated. Multiple passes of map features may be made by mobile sensor platforms and the results processed. As a result, sensor data values for particular map features may be aggregated over time. The average, mean, standard of deviation and/or other statistical values may also be calculated for each pass. A total average, total mean, total standard of deviation and/or other total statistical values may be calculated for all data collected for each map feature using the average, mean, standard of deviation and/or other statistical values for each pass of the map feature. Thus, statistical values may be updated as additional sensor data is captured and processed for subsequent passes. In some embodiments, the sensor data values may be processed to provide additional information, at 416. For example, an environmental score indicating the environmental quality and confidence score may also be calculated. Thus, the data values may be further processed in order to facilitate individuals' access to and understanding of the environmental data.

For example, suppose mobile sensor platform 102A traverses a route in map 300 shown in FIG. 5A. Also suppose that road segments 340 are used as map features. Each road segment 340 has a length of thirty meters in this example. In some embodiments, the size of each road segment may be selected so that the time taken to traverse the road segment at an appropriate speed (e.g. within a threshold of a speed limit—such as 25 mph±5 mph) is sufficient for the sensor to accurately gather sensor data for at least one sensor data point per road segment. Thus, the length of the road segment for a sensor may be set so that at least one time interval for the sensor passes before the sensor platform traverses the road segment. In some embodiments, the lengths of road segments may be selected so that the sensor can collect data for multiple data points per road segment when traveling at the appropriate speed. In some embodiments, the length of the road segment is selected so that all sensors on the sensor platform can collect data for one or more observations (e.g. road segment is sufficiently long that at least one time interval for the slowest sensor expires while the platform is still within the road segment). Thus, in some embodiments, the length of segment is chosen conservatively to obtain an adequate number data points collected to report a value for each segment. For example, the segment length might be selected to be one hundred meters in such a case. The segment length might be shortened and a number of expected data points derived based on the range of anticipated speeds as indicated above. However, averaging in multiple dimensions (averaging per pass, and by averaging several of those "per-pass averages" to create a representative final result) may allow for the use of longer segments and obviate the use of anticipated speeds to derive the expected number of data points for sensors. Sensor and position data are captured using method 200 and received by server 150 at 402 and 404. Suppose the sensor data for a particular sensor 110 over a portion of the route is given by Table 1. This may be the data received by server 150 at 402. As can be seen in Table 1, sensor 110 captures data every second and the first data point is captured at time t1.

TABLE 1

| Timestamp | Sensor Data (kΩ) |
|---|---|
| t1 | 4.669 |
| t1 + 1 seconds | 4.728 |
| t1 + 2 seconds | 4.730 |
| t1 + 3 seconds | 4.789 |

At 404, server 150 receives position data from GPS unit 145. Suppose that the GPS data is given by Table 2. For simplicity, the GPS data is simply indicated as starting at Position 1 and adding a distance and direction. For clarity, the first GPS data point is also shown as occurring at t1, the same time that the first data point is sensed. However, the first GPS data point need not be at the same time as the first sensor data point. Instead, a GPS data point that has a timestamp close to Position 1 might be used. Position 1 is shown in FIG. 5A as a black circle and labeled P1. Also suppose that P1 is eight meters from the boundary between road segment 340-1 and road segment 340-2. For the purposes of the example, the difference in time between the first sensor data point and the first GPS point is 0.2 seconds. In this example, GPS unit 145 gathers GPS data every 0.5 second.

TABLE 2

| Sensor Timestamp | GPS Data |
|---|---|
| t1 | Position 1 |
| t1 + .5 second | Position 1 + 6 meters west |
| t1 + 1 second | Position 1 + 11 meters west |
| t1 + 1.5 seconds | Position 1 + 25 meters north |
| t1 + 2 seconds | Position 1 + 19 meters west |
| t1 + 2.5 seconds | Position 1 + 25 meters west |
| t1 + 3 seconds | Position 1 + 32 meters west |

The GPS data shown in Table 2 is used to generate trajectories and corrected location(s) at 406. As can be seen in Table 2, the trajectory is westward at approximately twenty-five miles per hour. However, for time t1+1.5 seconds, the position is radically different than for the 0.5 seconds before and after this time. Consequently, at 406, the corrected position for this position timestamp is generated. Based on the trajectory and position, this is position is updated to a corrected location of Position 1+15 meters west. This is shown in Table 3. The corrected location is shown in italics.

TABLE 3

| Position Timestamp | GPS Data |
|---|---|
| t1 | Position 1 |
| t1 + .5 second | Position 1 + 6 meters west |
| t1 + 1 second | Position 1 + 11 meters west |
| t1 + 1.5 seconds | *Position 1 + 15 meters west* |
| t1 + 2 seconds | Position 1 + 19 meters west |
| t1 + 2.5 seconds | Position 1 + 25 meters west |
| t1 + 3 seconds | Position 1 + 32 meters west |

The position data points are assigned to map features 340 based on the position timestamps and corrected locations. The position timestamps and corresponding map features are shown in Table 4.

TABLE 4

| Position Timestamp | Map Feature |
|---|---|
| t1 | 340-1 |
| t1 + .5 second | 340-1 |
| t1 + 1 second | 340-2 |
| t1 + 1.5 seconds | 340-2 |
| t1 + 2 seconds | 340-2 |
| t1 + 2.5 seconds | 340-2 |
| t1 + 3 seconds | 340-2 |

At 410, sensor data is processed to provide sensor values. In some embodiments, 410 may occur substantially in parallel with 406 and 408. After 410, the sensor data value may be given in Table 5.

TABLE 5

| Timestamp | Sensor Data Values (ppm) |
|---|---|
| t1 | 8.2 |
| t1 + 1 seconds | 8.3 |
| t1 + 2 seconds | 8.3 |
| t1 + 3 seconds | 8.4 |

At 412, the sensor data values are assigned to map features corresponding to the positions of mobile sensor platform 102A that are in the same time interval. For this sensor having a time interval of one second, GPS data within 0.5 seconds of the sensor timestamp is considered to be in the same interval. Thus, the first point of the GPS data is in the same interval as the first point of sensor data. The second and third points of GPS data are in the same interval as the second sensor data point. The fourth and fifth points of GPS data are in the same interval as the third sensor data point. The sixth and seventh points of GPS data are in the same interval as the fourth sensor data point. Based on the GPS data and timing shown, the second sensor value is place in road segment 340-2.

TABLE 6

| Map Feature (Road Segment) | Sensor Data Values (ppm) |
|---|---|
| 340-1 | 8.2 |
| 340-2 | 8.3 |
| 340-2 | 8.3 |
| 340-2 | 8.4 |

Thus, sensor data may be associated with map features. In some embodiments, a mean, standard of deviation and/or average may be provided for each map feature that includes multiple sensor data values. In the example above, segment 340-2 may be assigned a mean/average value of 8.3. In addition, sensor data from stationary sensor platforms 103/311 may be incorporated into the assignment of sensor data values for particular map features. The process may be repeated for data from other passes using the same route 330 or other routes, such as 332, at 414. In some embodiments, the mean, average, standard deviation and/or other statistical values may be updated and assigned to the map features. Thus, data may be aggregated over time to provide increased confidence in the environmental data presented. At 416, various scores may also be determined for each road segment.

Using method 400, a sparse network of mobile sensor platforms 102A, 102B and 102C may provide hyper-local environmental data. Because mobile sensor platforms 102A, 102B and 102C are used and may make multiple passes over a region, fewer sensor platforms are required to obtain a sufficient amount of sensor and position data. Sensor data and position data may be collected at a relatively high frequency in comparison with the speeds at which the vehicles (and thus mobile sensor platforms 102A, 102B and 102C) traverse the route. Consequently, one or more sensor data points may be assigned per map feature. Map features may be relatively small and, therefore, hyper-local in nature. For example, sensor data values may be assigned to road segments that are not longer than two hundred meters in some embodiments. In some embodiments, sensor data values may be assigned to road segments that are not longer than one hundred meters. In some such embodiments, sensor data values may be assigned to road segments that are not longer than thirty meters. In some embodiments, the road segments may be twenty-five meters or less. Thus, changes in sensor data values on a scale of one hundred meters or less may be determined. Hyper-local variations in the sensor data may be determined. Further, the sensor data values may be further processed to generate scores or other indicia of environmental quality that can vary on the same scale as the map features. Thus, hyper-local variations in environmental quality may be determined.

Figure 6:
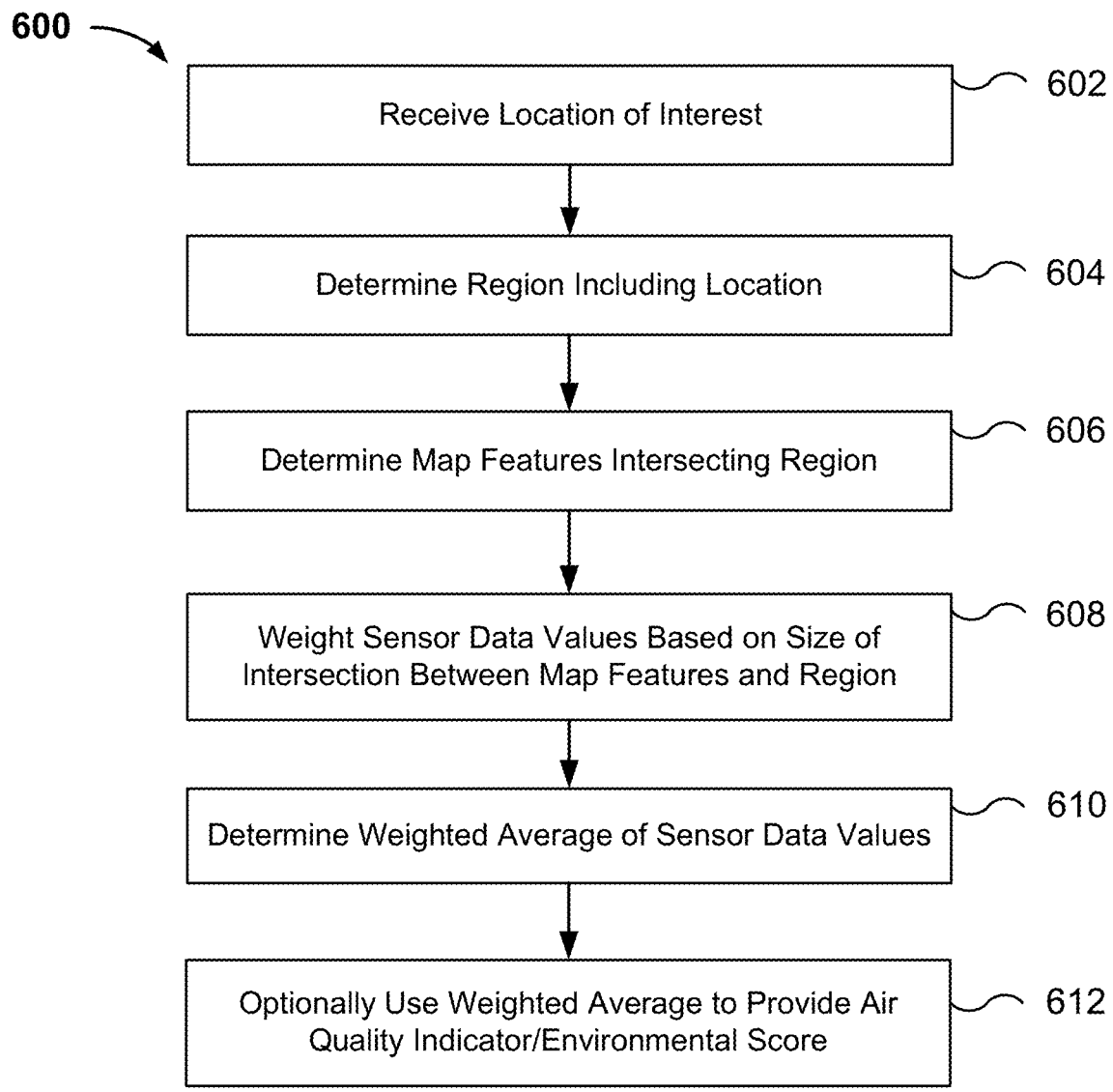
FIG. 6 depicts an embodiment of a method for providing environmental data for a particular location.

FIG. 6 depicts an embodiment of method 600 for providing environmental data for a particular location. Method 600 is described in the context of system 100 and map 300. However, method 600 may be used in connection with other data collection and/or processing systems. For clarity, only some portions of method 600 are shown. Although shown in a sequence, in some embodiments, processes may occur in parallel and/or in a different order. Method 600 generates environmental data for a map location based on the sensor data values assigned to map features proximate to the map location. In some embodiments, any sensor data values assigned to the map location are also used.

The map location of interest is received, at 602. In some embodiments, the map location is received from a user. The map location may be a map feature (e.g. an identified road segment or cell) and/or other location which may not have sensor data values explicitly assigned. For example, the location may be an address. In some embodiments, the map location may be a neighborhood, a specified set of addresses, a city or other set of geographic location(s) specified. Thus, the location received at 602 is desired to be associated with one or more nearby map features.

A region that includes the map location is defined, at 604. In some embodiments, the region may be defined as all areas within a particular radius of the center or latitude/longitude coordinates of the map location. In some embodiments, the region may include all areas within a particular distance from the perimeter of the map location. Other regions may be defined in other embodiments. The map features that intersect the region are determined, at 606. In some embodiments, a map feature that has any portion included in the region is identified at 606. In other embodiments, the map features intersecting the region may be determined in another manner. For example, only map features completely within the region might be determined as intersecting the region at 606.

The sensor data values for the map features intersecting the region may be weighted based upon their intersection, at 608. For example, in some embodiments, the map features are weighted based upon the fraction of their area intersecting the region. Map features having a larger area within the region have a higher weight. In some embodiments, map features closer to the map location (e.g. closer to the center of the region) may have a higher weight. Additional and/or other criteria may be used to weight the sensor data values.

A weighted average of the sensor data values for the map features intersecting the region is determined for each sensor of interest, at 610. Thus, environmental data for the map location can be generated. In some embodiments, an environmental score or other indicia of environmental quality may be calculated for the map location based on the weighted average(s) at 612.

Figure 7:
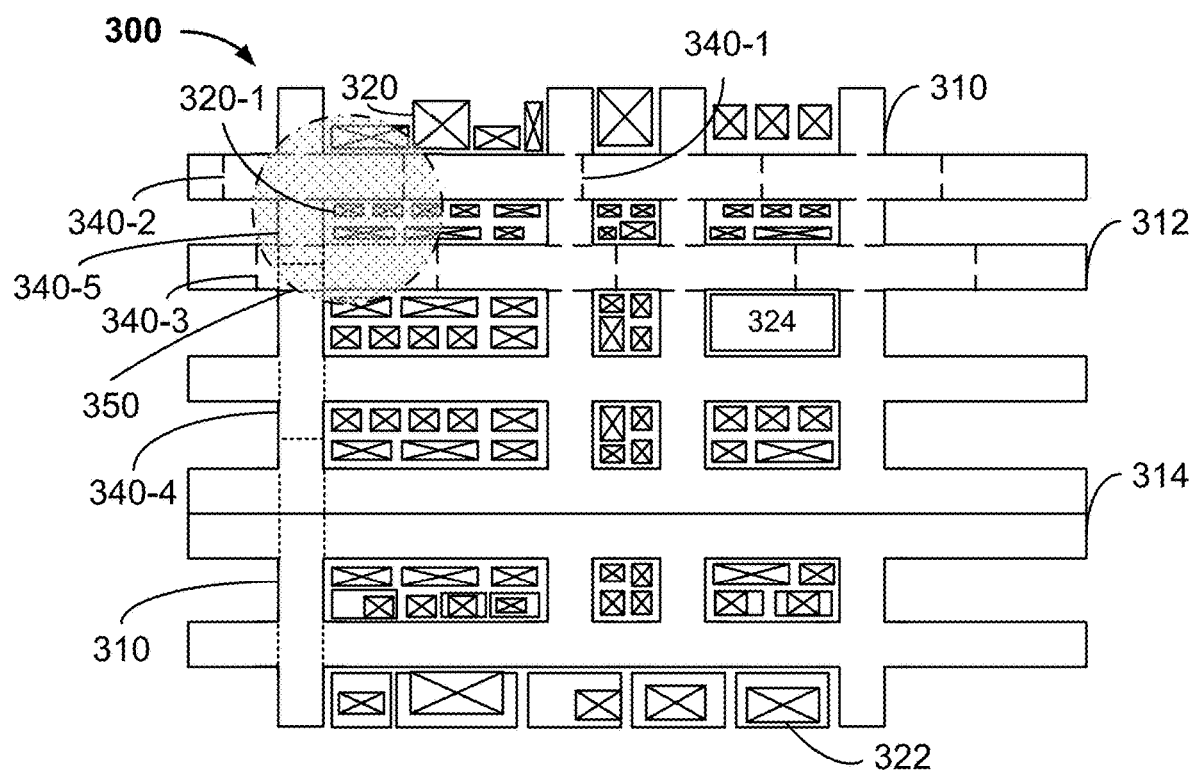
FIG. 7 depicts an embodiment of a particular location and the surrounding map features.

For example, FIG. 7 depicts an embodiment of a particular location and the surrounding map features on map 300 for which environmental data is desired to be generated using method 600. The map location is the address for structure 320-1. Thus, the address for structure 320-1 is received by server 150, at 602. Server 150 determines the region including the map location 320-1 at 604. In the embodiment shown, region 350 is defined at 604. Region 350 is a circle centered on map location 320-1. For clarity, region 320-1 is shown partially filled and with a dotted-dashed perimeter.

The map features shown in map 300 for FIG. 7 are road segments 340. Vertical road segments are shown bounded by dotted lines, while horizontal road segments are bounded by dashed lines. For simplicity, not all road segments are labeled or delineated by dashed or dotted lines. At 606, road segments 340-1, 340-2, 340-2, 340-4 and 340-5 are determined to intersect region 350. Horizontal road segments 340-1, 340-2 and 340-3 and vertical road segments 340-4 and 340-5 intersect region 350 to varying degrees. Thus, at 608, the sensor data values assigned to road segments 340-1, 340-2, 340-2, 340-4 and 340-5 are weighted. In some embodiments, road segment 340-3 has the highest weight because the largest fraction of road segment 340-3 intersects region 350.

Weighted averages of the sensor data values for road segments 340-1, 340-2, 340-2, 340-4 and 340-5 are determined at 610. If map location 320-1 had sensor data values assigned, for example because of a stationary sensor platform within map location 320-1, then these sensor data values may also be weighted at 608 and included in the calculations of 610. Thus, environmental data for map location 320-1 may be generated. This environmental data may then be presented and/or otherwise used to assess the environmental quality at map location 320-1.

Thus, using method 600, sensor data values assigned to surrounding map features may be interpolated to obtain sensor data values for an address or other map locations. As discussed above, the sensor data values and map features are hyper-local in nature. Consequently, the sensor data values generated for the map location are also hyper-local. Thus, the environmental data specific to the map location may be provided. Adjacent addresses (e.g. adjacent map locations) may have different sensor data values generated using method 600 because different map features may intersect the regions corresponding to the adjacent addresses. As a result, a user may be able to investigate the environmental quality particular to their address.

Figures 8, 9:
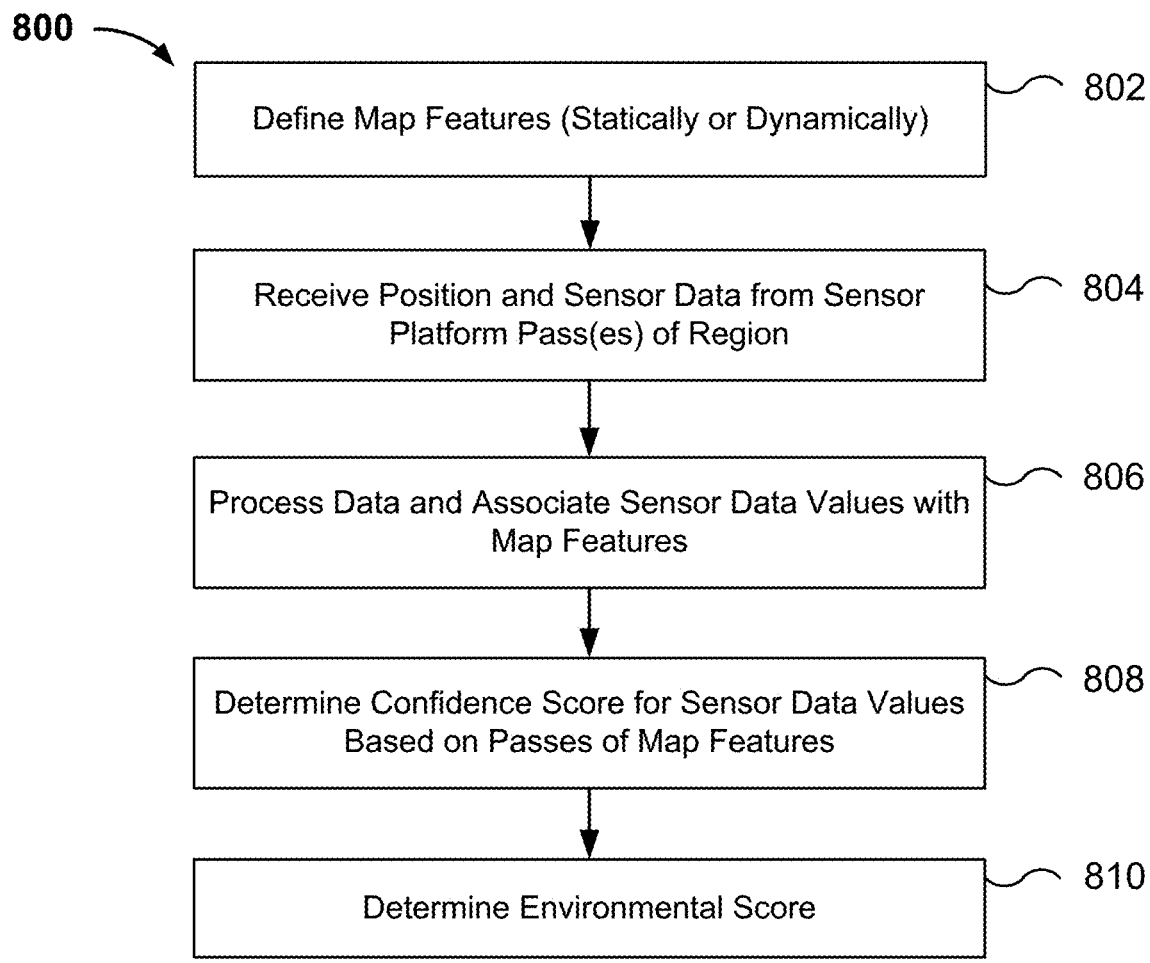
FIG. 8 depicts an embodiment of a method for providing additional information associated with environmental data and map features.
FIG. 9 depicts an embodiment of a score presentation.

FIG. 8 depicts an embodiment of method 800 for providing a score associated with environmental data and map features. Method 800 is described in the context of system 100 and map 300. However, method 800 may be used in connection with other data collection and/or processing systems. For clarity, only some portions of method 800 are shown. Although shown in a sequence, in some embodiments, processes may occur in parallel and/or in a different order. Method 800 may be used to allow laymen to more easily understand environmental data associated with their address, neighborhood or city.

The map features may be defined, at 802. For example, the road segment length may be specified for each sensor, for particular regions or in another matter. As discussed above, the map feature length and/or area are selected at 802 such that sensor data can be accurately captured at least once per map feature. In some embodiments, the size of the map feature is selected to ensure an adequate number data points is collected to report a value for each sensor in each map feature. In such embodiments, averaging per pass combined with averaging several of the "per-pass averages" (for the multiple passes) may be used to provide representative values for such segments. The sensor data and position data are received from multiple passes over an area of interest, at 804. The sensor and position data are processed and sensor data values associated with map features at 806. For example, 804 and 806 may correspond to some or all of methods 200 and 400.

A confidence score is determined for the sensor data values, at 808. In some embodiments, the confidence score is based on the number of passes for the map features, region, map location or other area of interest. A higher number of passes may result in a higher confidence score. For example, it may be determined that a particular number of passes, such as twenty, is sufficient to describe the environmental data. In such an embodiment, the confidence level may be a percentage of twenty passes that have been completed. If five passes have been completed, then a confidence score of twenty-five percent may be calculated at 808. In some embodiments, the amount of noise in sensor data, the time between passes, weather conditions, pollution anomalies (e.g. wild fires and/or other singular events) and/or other criteria may be incorporated into the confidence score.

An environmental score is calculated for the region of interest, at 810. If the region of interest is a map location, then method 600 may also be performed in order to generate the sensor data values used in determining an environmental score. In some embodiments, the environmental score is calculated for each map feature (e.g. each road segment). In some embodiments, the environmental score may be calculated at 810 for each pollutant or other condition such as temperature measured. For example, the environmental score for each pollutant may be determined scaled upon a maximum score of one hundred and a minimum score of zero, where the lowest value of the pollutant for a particular area corresponds to one hundred. Thus, each pollutant may be normalized with respect to data collected for the same area, such as the same city. In some embodiments, an overall score may be calculated based upon some or all of the pollutants measured. For example, the normalized scores for each pollutant may be averaged. In other embodiments, the environmental score may be determined in another manner.

For example, each road segment/map feature or map location may be ranked. The ranks may be normalized or averaged to obtain a comparison. In some embodiments, the environmental score is calculated based upon standards, such as governmental standards for the maximum desirable amounts of particular pollutants or conditions. In some embodiments, the sensor data values may be weighted. For example, particulate matter may be of greater interest in environmental quality. Thus, sensor data values for particulate matter may have a higher weight. In some embodiments, a ranking and government standards may be combined to provide the score. In some embodiments, the score may numeric (as discussed above) and/or may be a non-numeric categorical variable. For example, red may be used for poor/unhealthy environmental quality, yellow for moderate environmental quality and blue for good environmental quality, where "poor/unhealthy", "moderate" and "good" are categories having corresponding numeric score ranges for selected sensor data values (e.g. ranges for particulate matter having a diameter of less than 2.5 micrometers (PM2.5), $NO_2$, noise, temperature and $O_3$).

FIG. 9 depicts an embodiment of the environmental score 900 as presented to the user and provided using method 800. Although particular pollutants are shown, other pollutants and/or conditions might be included. For example, noise levels, radiation levels, temperatures (e.g. to indicate whether the user is in a heat island) and/or other conditions could be included in environmental score 900 in other embodiments. Environmental score 900 includes a table as well as other indicators. The location for environmental score 900 is shown. Each pollutant for environmental score 900 is indicated in the table. Both the sensor data values and the corresponding normalized score are provided. Thus, an absolute indicator of the amount of the pollutant (sensor data value) and a relative score are both provided. An overall (final) score is provided. Also shown is a confidence score. An emoji (e.g. a particular non-numeric categorical value) indicating whether the score is good, mid-range or poor is shown. The range of dates for which sensor data were collected for the score is also shown.

Using method 800 and environmental score 900, data may be presented to a user in an easily digestible fashion. For example, a user may view environmental score 900 and gain an understanding of whether their environmental quality is good or poor without understanding the meaning of individual sensor data values. Thus, environmental data collected, processed and analyzed as described herein may be more readily used by individuals and communities.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for associating environmental data with map features, comprising:
receiving sensor data associated with each of a plurality of time intervals from a sensor on a mobile sensor platform, the sensor measuring at least one of a pollutant, a contaminant, or a time-varying component of air at the mobile sensor platform, wherein the receiving of the sensor data associated with each of a plurality of time intervals from the first sensor on a mobile sensor platform comprises:

receiving, associated with a first pass, a first sensor data associated with each of the plurality of time intervals from the sensor on the mobile sensor platform;

receiving position data associated with the plurality of time intervals from the mobile sensor platform;

generating trajectories and corrected locations of the mobile sensor platform for the plurality of time intervals using the position data, comprising:
  establishing a trajectory based on position timestamps and GPS data points; and
  generating a corrected location based on the established trajectory and other GPS data;

assigning a position of the mobile sensor platform to a corresponding map feature for each of the plurality of time intervals based on the trajectories and corrected locations;
  processing the sensor data to generate sensor data values for each of the plurality of time intervals, the sensor data values including at least one value for the at least one of the pollutant, the contaminant, or the time-varying component of the air, wherein the processing of the sensor data to generate the sensor data values for each of the plurality of time intervals comprises: processing the first sensor data to generate a first sensor data value;

assigning the sensor data values to the corresponding map feature of the position of the mobile sensor platform for each of the plurality of time intervals, the at least one value for the at least one of the pollutant, the contaminant, or the time-varying component of the air being assigned to the corresponding map feature; and repeating the sensor data receiving, position data receiving, trajectories generating, position assigning, sensor data processing and assigning sensor data values for a plurality of passes of the corresponding map feature, wherein the plurality of passes includes the first pass and a second pass, wherein:
  the repeating of the sensor data receiving comprises:
    receiving, associated with the second pass, a second sensor data associated with each of the plurality of time intervals from the sensor on the mobile sensor platform;
  the repeating of the sensor data processing comprises:
    processing the second sensor data to generate a second sensor data value; and
  the repeating of the assigning of the sensor data values for the plurality of passes of the corresponding map feature comprises:
    combining the first sensor data value with the second sensor data value to obtain the sensor data values;
wherein the corresponding map feature has a size based on the sensor that provides the sensor data for the at least one of the pollutant, the contaminant, or the time-varying component of the air.

2. The method of claim 1, further comprising:
generating the environmental data for a map location based on the sensor data values assigned to the corresponding map feature for a plurality of map features proximate to the map location.

3. The method of claim 2, wherein the plurality of map features are within a particular distance of the map location, and wherein the generating the environmental data further includes:
  weighting the sensor data values for each of the plurality of map features.

4. The method of claim 1, wherein the corresponding map feature is selected from a road segment and a cell.

5. The method of claim 4, wherein the road segment has a road segment length corresponding to the size and the cell has an area corresponding to the size, the road segment length being a dynamic length, the cell area being a dynamic cell area.

6. The method of claim 5, wherein the dynamic length is generated based on the sensor corresponding to the sensor data value.

7. The method of claim 1, further comprising:
determining an environmental score for the corresponding map feature based on the sensor data values for each of the plurality of passes.

8. The method of claim 1, further comprising:
determining a confidence score for the sensor values of the corresponding map feature based on the plurality of passes.

9. The system of claim 1, wherein the corresponding map feature is a road segment having a length not exceeding thirty meters.

10. A system for associating environmental data with map features, comprising:
  a processor configured to:
    receive sensor data associated with each of a plurality of time intervals from a sensor on a mobile sensor platform, the sensor measuring at least one of a pollutant, a contaminant, or a time-varying component of air at the mobile sensor platform, wherein the receiving of the sensor data associated with each of a plurality of time intervals from the first sensor on a mobile sensor platform comprises to:
      receiving, associated with a first pass, a first sensor data associated with each of the plurality of time intervals from the sensor on the mobile sensor platform;
    receive position data associated with the plurality of time intervals from the mobile sensor platform;
    generate trajectories and corrected locations of the mobile sensor platform for the plurality of time intervals using the position data, comprising to:
      establish a trajectory based on position timestamps and GPS data points; and
      generate a corrected location based on the established trajectory and other GPS data;
    assign a position of the mobile sensor platform to a corresponding map feature for each of the plurality of time intervals based on the trajectories and corrected locations, the corresponding map feature having a size based on the sensor that provides the sensor data for the at least one of the pollutant, the contaminant, or the time-varying component of the air;
    process the sensor data to generate sensor data values for each of the plurality of time intervals, the sensor data values including at least one value for the at least one of the pollutant, the contaminant, or the time-varying component of the air, wherein the processing of the sensor data to generate the sensor data values for each of the plurality of time intervals comprises to:
    process the first sensor data to generate a first sensor data value; and assign the sensor data values to the corresponding map feature of the position of the mobile sensor platform for each of the plurality of time intervals, the at least one value for the at least one of the pollutant, the contaminant, or the time-varying component of the air being assigned to the corresponding map feature; and repeat the sensor data receiving, position data receiving, trajectories generating, position assigning, sensor data processing and assigning sensor data values for a plurality of passes of the corresponding map feature, wherein the plurality of passes includes the first pass and a second pass, wherein:
the repeating of the sensor data receiving comprises to:
receive, associated with the second pass, a second sensor data associated with each of the plurality of time intervals from the sensor on the mobile sensor platform;
the repeating of the sensor data processing comprises to:
process the second sensor data to generate a second sensor data value; and the repeating of the assigning of the sensor data values for the plurality of passes of the corresponding map feature comprises to:
combine the first sensor data value with the second sensor data value to obtain the sensor data values; and
a memory coupled to the processor and configured to provide the processor with instructions.

11. The system of claim 10, wherein the processor is further configured to:
generate the environmental data for a map location based on the sensor data values assigned to the corresponding map feature for a plurality of map features proximate to the map location.

12. The system of claim 11, wherein the plurality of map features are within a particular distance of the map location and wherein to generate the environmental data the processor is further configured to:
weighting the sensor data values for each of the plurality of map features.

13. The system of claim 10, wherein the corresponding map feature is selected from a road segment and a cell.

14. The system of claim 13, wherein the road segment has a road segment length corresponding to the size and the cell has an area corresponding to the size, the road segment length is a dynamic length and the cell area is a dynamic cell area.

15. The system of claim 14, wherein the dynamic length is generated based on the at least one sensor corresponding to the sensor data value.

16. The system of claim 10, wherein the processor is further configured to:
determine an environmental score for the corresponding map feature based on the sensor data values for each of the plurality of passes.

17. The system of claim 10, wherein the processor is further configured to:
determine a confidence score for the sensor values of the corresponding map feature based on the plurality of passes.

18. A computer program product for associating environmental data with map features, the computer program product being embodied in a non-transitory computer readable storage medium and comprising computer instructions for:
receiving sensor data associated with each of a plurality of time intervals from a sensor on a mobile sensor platform, the sensor measuring at least one of a pollutant, a contaminant, or a time-varying component of air at the mobile sensor platform, wherein the receiving of the sensor data associated with each of a plurality of time intervals from the first sensor on a mobile sensor platform comprises:
receiving, associated with a first pass, a first sensor data associated with each of the plurality of time intervals from the sensor on the mobile sensor platform;
receiving position data associated with the plurality of time intervals from the mobile sensor platform;
generating trajectories and corrected locations of the mobile sensor platform for the plurality of time intervals using the position data, comprising:
establishing a trajectory based on position timestamps and GPS data points; and
generating a corrected location based on the established trajectory and other GPS data;
assigning a position of the mobile sensor platform to a corresponding map feature for each of the plurality of time intervals based on the trajectories and corrected locations, the corresponding map feature having a size based on the sensor that provides the sensor data for the at least one of the pollutant, the contaminant, or the time-varying component of the air;
processing the sensor data to generate sensor data values for each of the plurality of time intervals, the sensor data values including at least one value for the at least one of the pollutant, the contaminant, or the time-varying component of the air, wherein the processing of the sensor data to generate the sensor data values for each of the plurality of time intervals comprises:
processing the first sensor data to generate a first sensor data value; assigning the sensor data values to the corresponding map feature of the position of the mobile sensor platform for each of the plurality of time intervals, the at least one value for the at least one of the pollutant, the contaminant, or the time-varying component of the air being assigned to the corresponding map feature; and
repeating the sensor data receiving, position data receiving, trajectories generating, position assigning, sensor data processing and assigning sensor data values for a plurality of passes of the corresponding map feature, wherein the plurality of passes includes the first pass and a second pass, wherein:
the repeating of the sensor data receiving comprises:
receiving, associated with the second pass, a second sensor data associated with each of the plurality of time intervals from the sensor on the mobile sensor platform;
the repeating of the sensor data processing comprises:
processing the second sensor data to generate a second sensor data value; and
the repeating of the assigning of the sensor data values for the plurality of passes of the corresponding map feature comprises:
combining the first sensor data value with the second sensor data value to obtain the sensor data values.

19. The method of claim 18, wherein the pollutant is an air pollutant, the contaminant is an air contaminant, and the at least one value assigned to the corresponding map features is for at least one of the air pollutant, the air contaminant, or the time-varying component of the air.

* * * * *

UNITED STATES PATENT AND TRADEMARK OFFICE
CERTIFICATE OF CORRECTION

PATENT NO. : 11,719,541 B2
APPLICATION NO. : 16/682871
DATED : August 8, 2023
INVENTOR(S) : Todd Langland et al.

It is certified that error appears in the above-identified patent and that said Letters Patent is hereby corrected as shown below:

On the Title Page

Column 2, item (56), other publications, cite no. 1, delete "Pullution" and insert --Pollution--, therefor.

In the Specification

In Column 6, Line(s) 35, delete "CH4" and insert --$CH_4$--, therefor.

In Column 8, Line(s) 61, after "captured from", delete "by".

In Column 13, Line(s) 1, after "number", insert --of--.

In Column 17, Line(s) 22, after "number", insert --of--.

Signed and Sealed this
Seventh Day of November, 2023

Katherine Kelly Vidal
*Director of the United States Patent and Trademark Office*